United States Patent [19]

Smid et al.

[11] Patent Number: 5,124,079

[45] Date of Patent: Jun. 23, 1992

[54] AMIDATED FATTY ACID MIXTURES AND USE THEREOF AS THICKENERS

[75] Inventors: Jacob K. Smid, Doetinchem; Reinout H. van der Veen, Arnhem, both of Netherlands

[73] Assignee: DSM N.V., Heerlen, Netherlands

[21] Appl. No.: 485,873

[22] Filed: Mar. 1, 1990

[30] Foreign Application Priority Data

Mar. 4, 1989 [NL] Netherlands ............... 8900539

[51] Int. Cl.$^5$ ............... C11D 3/32; C11C 1/02; C11C 3/00
[52] U.S. Cl. ............... 252/548; 252/174.21; 252/174.22; 252/579; 252/544; 554/61; 554/64
[58] Field of Search ......... 252/529, 544, 548, 174.21, 252/174.22; 260/404

[56] References Cited

U.S. PATENT DOCUMENTS

| | | | |
|---|---|---|---|
| 4,072,622 | 2/1978 | Kühling et al. | 252/179 |
| 4,169,075 | 9/1979 | Kühling et al. | 252/558 |
| 4,179,391 | 12/1979 | Kaufmann et al. | 252/99 |
| 4,312,771 | 1/1982 | Matsuda et al. | 252/107 |
| 4,438,012 | 3/1984 | Kühling et al. | 252/131 |

FOREIGN PATENT DOCUMENTS

| | | |
|---|---|---|
| 0219893 | 4/1987 | European Pat. Off. . |
| 1618397 | 7/1970 | Fed. Rep. of Germany . |
| 62-10197 | 1/1987 | Japan . |
| 62-10199 | 1/1987 | Japan . |
| 62-57495 | 3/1987 | Japan . |

OTHER PUBLICATIONS

European Search Report and Annex, Application No. 90200463.9.
McCutcheon's Emulsifiers and Detergents 1983 North American Edition pp. 133, 149, 178, 194, 234.
Industrial Oil and Fat Products; Alton E. Bailey; 1945 pp. 157, 167, 172.
Akzo Chemicals GmbH, Niederlassung Emmerich, Oelwerke, Noury and van der Lande (1985), pp. 1-16.

*Primary Examiner*—A. Lionel Clingman
*Assistant Examiner*—Erin Higgins
*Attorney, Agent, or Firm*—Cushman, Darby & Cushman

[57] ABSTRACT

The invention relates to mixtures of amidated fatty acids or derivatives thereof of the general formula

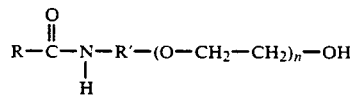

wherein R' is absent or an alkyl group with 2-4 C-atoms, the average value of n is 0,5 to 3 and R represents a fatty acid radical with 14-24 C-atoms obtained from oils produced from the plant species 'Brassica' with an eruca acid content lower than 5%.

These products are good thickeners for surfactants and/or detergents. No nitrose compounds of (di)alkanolamines, which could present a health hazard, are formed in the thickeners according to the invention.

8 Claims, No Drawings

AMIDATED FATTY ACID MIXTURES AND USE THEREOF AS THICKENERS

The present invention relates to mixtures of amidated fatty acids or derivatives thereof, to thickeners consisting of or containing such mixtures, to the use of such thickners to 'thicken' products containing surfactants and/or detergents and to surfactants and/or detergents containing such thickeners.

Mixtures of amidated fatty acids from e.g. rape oil or derivatives thereof are described in GB 420,545 (1932). The rape oil produced in those days from the plant species 'brassica' however suffered from a high content of eruca acid. In 'Analyse en Warenkennis der voornaamse vette Lichamen', Dr. Ir. F. H. van Leent edited by D. B. CENTEN's Uitgevers-Maatschappij (N.V.) Amsterdam (1934), p. 183-185 a eruca acid content is described of 47-52 5% and in Ullmann 7, pp. 472-473 and 12, p. 242 (1956), ed. Urban Schwarzenberg (Müchen-Berlin), a content of 50%. In food industry eruca acid is qualified as suspicious. The same yields for the cosmetic industry. Later on plants belonging to the plant species 'brassica' are developed with much lower eruca acid content.

The use of thickeners in surfactants and/or detergents, such as shampoos, shower and bath foams, lotions, dishwashing agents, etc., is commonly known. For various reasons it is desirable that surfactants and/or detergents have a certain 'substance' and therefore they are 'thickened' where necessary by the addition of thickeners. Common thickeners are fatty acid dialkanolamides, in particular fatty acid diethanolamides, which are mentioned in, for instance, a publication by H. Hensen et al. in the reports of the '2nd World Surfactant Congress', organised by ASPA (Syndicat National des Fabricants d'Agents de Surface et de Produits Auxiliaires Industriels) from May 24 to 27, 1988, at Paris, part (Volume) II, pp 378-398.

As fatty acid diethanolamide use is made of, in particular, coconut fatty acid diethanolamide, which is commercially available, for example under the tradename 'Comperlan KD'.

The fatty acid from which the fatty acid dialkanolamide is derived is usually a mixture of fatty acids with a composition corresponding to the fatty acid composition of an oil. The fatty acid diethanolamides are usually prepared by hydrolysing an oil and converting the fatty acids formed in the hydrolysis with diethanolamine, or by converting the oil with diethanolamine in one step, which is also known as 'aminolysis'. The known coconut fatty acid diethanolamide can be prepared by aminolysing coconut oil with diethanolamine. A fatty acid diethanolamide in general and coconut fatty acid diethanolamide in particular usually still contains small amounts of unconverted diethanolamine, which is capable of forming N-nitrosodiethanolamine with nitrosating compounds. Examples of compounds with a nitrosating effect in this context are: nitrogen oxides, nitrites in aqueous solutions at low pH values and nitrosating preservatives such as: 2-bromo-2-nitropropane-1,3-diol and 5-bromo-5-nitro-1,3-dioxane. It has been found that N-nitrosodiathanolamine has carcinogenic properties. In view of this, the allowable concentrations of N-nitrosodiethanolamine are constantly being reduced and in West Germany the Bundesgesundheitsamt has recently advised against using diethanolamine in the preparation of cosmetics and the like. It may therefore be assumed that the use of a thickener like coconut fatty acid diethanolamide will be forbidden in the near future.

New amidated fatty acid mixtures have now been found which consist substantially of compounds of fatty acid radicals with 14-24 carbon atoms obtained from oils produced from crops of the plant species 'Brassica', with an eruca acid content lower than 5%.

It has been found—and that is another aspect of the invention—that the amidated fatty acid mixtures according to the invention are good thickeners or can be processed, as compounds with a thickening effect, to form thickeners. They may be mixed with mixtures of other thickeners such as low ethoxylated fatty alcohols.

The invention further comprises products containing surfactants and/or detergents containing one or more thickeners according to the invention—and this constitutes yet another aspect of the invention.

The amidated fatty acid mixtures according to the invention can be easily prepared, in a manner known per se, by converting esters of the aforementioned fatty acids in the form of an oil, produced from crops of the plant species 'Brassica', into monoalkanolamides, in particular into monoethanolamides and/or monoisopropanolamides and then ethoxylating the monoalkanolamides. These mixtures contain amidated fatty acids or derivatives thereof the general formula

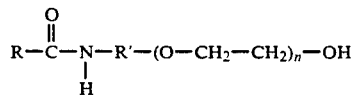

wherein $R'$ =absent or an alkyl rest with 2-4 C-atoms. The monoalkanolamides obtained as an intermediate will usually contain small amounts of residual monoalkanolamine. The residual monoalkanolamine may still contain traces of dialkanolamine. These small amounts of residual monoalkanolamine and any traces of dialkanolamine are completely converted in the subsequent ethoxylation. Hence there is absolutely no risk of the formation of nitrosamines as is the case with the known fatty acid diethanolamides.

Particularly good results are obtained with aminolysed fatty acid mixtures of the formula

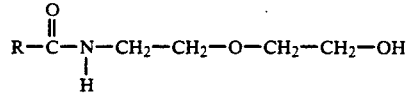

corresponding with a mixture of compounds containing exactly one ethoxy group ($n=1$ in the general formula) and $R'$ is ethyl. Such a mixture can be prepared by aminolysing rape oil (or derivatives thereof) with 2-(2-aminoethoxy)ethanol in a manner known per se.

These mixtures show the best results with respect to viscosity enhancement.

Monoalkanolamides of the fatty acid mixtures to be used according to the present invention, the fatty acids of which are predominantly unsaturated, are usually solids. However, it has been found that a small degree of ethoxylation, resulting in on average 0.5-3 and preferably 1-2 ethoxy groups, causes these monoalkanolamides to become pasty or liquid without affecting their thickening effect in an unacceptable manner. The small degree of ethoxylation usually causes a slight reduction in the thickening effect, but in the case of the thickeners discussed here this effect is still very satisfactory.

For the preparation of the thickeners discussed here use may be made of mixtures of largely unsaturated fatty acids, obtained by hydrolysis of oils produced from crops of the plant species 'Brassica'. These plants belong to the family of Cruciferae. The 'Brassica' plant species comprises different types of cabbage, but also mustard species, for which, besides the name 'Brassica', the name 'Sinapis' is sometimes also used. The best known oils produced from these species are rape oil and mustard-seed oil, which are obtained from plants, plant parts or plant seeds. Rape oil is obtained from, for instance, Brassica varieties such as Brassica Rapa L., *Brassica campestris* (rapeseed, cole-seed), mustard-seed oil is obtained from, for instance, *Brassica hirta*. Of course, the oils to be used are not limited thereto. Oils obtained from other varieties of Brassica species may also be used. Such oils can now be hydrolysed in a manner known per se. For the preparation of the monoethanolamides use may be made of the hydrolysate, which contains glycerol and other substances, without purification or concentration of the contained fatty acids, but it is equally possible to concentrate and/or purify the fatty acids in the hydrolysate or separate them from glycerol and use the product thus obtained. It is also possible to prepare the ethanolamides by directly 'aminolysing' a suitable oil in the presence of monoethanolamine as base. Both the product obtained in two steps and that obtained in one step by aminolysis can be directly processed further by ethoxylating it or by first completely or partially removing glycerol and/or other impurities from that product and ethoxylating the thus concentrated or purified product. Optionally, it is also possible to separate the ethoxylated glycerine from the ethoxylated fatty acid amide after ethoxylation.

Traces e.g. of dioxane and free ethylene oxide may be removed by steam, air or nitrogen.

The invention is further illustrated with the following examples, without however being limited thereby.

EXAMPLE I a) Aminolysis of rape oil with monoethanolamine (MEA)

885 grams of rape oil (Mw 900, estimated by saponification value) was mixed with 176 grams of MEA (98.0 eq.%) in a 2-l beaker equipped with a propeller mixer and a thermometer. The mixture was heated to 50° C. Then 8.4 grams of a 30% solution of sodium methylate in methanol was added. The heat of reaction caused the temperature to rise to 70° C. and the reaction mixture to become clear. After approximately 30 minutes the temperature was 80° C. The reaction mixture was maintained at 80° in an oven for one night, after which the degree of conversion was 93%.

b) Ethoxylation of amidated rape oil fatty acids 517 grams of the amidated fatty acids obtained according to a) was transferred to an autoclave. The air was expelled by purging with nitrogen, after which 197 grams of ethylene oxide was introduced under a vacuum. This caused the pressure to rise to 2.5-2.8 bar. After 20 minutes all of the ethylene oxide had been supplied. The pressure was maintained at 2.0 bar by introducing nitrogen, after which the mixture was stirred for 30 minutes.

Then the reaction mixture was discharged from the autoclave. The yield was 714 grams. The ethoxylated amidated rape oil fatty acids contained on average 1.6 ethylene oxide radicals.

EXAMPLE II a) Aminolysis of rape oil with monoethanolamine 3330 grams of rape oil (Mw 893) and 703 grams of MEA (103 eq.%) were introduced into a 5-l beaker equiped with a mixer and a thermometer, after which the mixture was heated to 50° C., with stirring. Then 40 grams of a 30% solution of $NaOCH_3$ in methanol was added. After 15 minutes the temperature had risen to 70° C. and the solution became clear. After 50 minutes the temperature had risen to 90° C. The reaction mixture was subsequently maintained at 70° C. in an oven. After 60 hours the degree of conversion was 98.6% (based on the MEA).

b) Ethoxylation of amidated rape oil fatty acids 2681 grams of amidated rape oil obtained according to a) was ethoxylated with 813 grams of ethylene oxide in an autoclave at 125° C., at a pressure of at most 3.0 bar. After all the ethylene oxide had been added the mixture was stirred for 30 minutes. The yield was 3494 grams. These ethoxylated amidated rape oil fatty acids contained on average 1.3 ethylene oxide radicals.

EXAMPLE III

Ethoxylation of amidated rape oil 2121 grams of rape oil fatty acids aminolysed according to the process described in example IIa) was ethoxylated with 1038 grams of ethylene oxide. The ethoxylation was carried out at approx. 125° C., at a pressure of 2.0-3.0 bar. The yield was 3159 grams of ethoxylated amidated rape oil. These ethoxylated amidated rape oil fatty acids contained on average 2.1 ethylene oxide racials.

EXAMPLE IV a) Aminolysis of rape oil with monoisopropanolamine (MIPA)

1313 grams of rape oil (Mw 885.5) was introduced into a 3-l beaker equiped with a propeller mixer and a thermometer. Monoisopropanolamine (337 grams, 102 eq.%) was added to this. The mixture was heated to 70° C. and at this temperature 13.1 grams of a 30 wt. % solution of sodium methylate in methanol was added. After about 10 minutes the temperature had risen to 75° C. and the turbid solution became clear. After 45 minutes the temperature was 85° C. The reaction mixture was then maintained at 80° C. for 24 hours, after which 78% amine had been converted. When the reaction mixture was maintained at 80° C. for another 3 days the degree of conversion of the amine increased to 91%.

b) Ethoxylation of the aminolysed rape oil fatty acid 897 grams of the aminolysed rape oil fatty acids obtained according to example IVa) was transferred to an autoclave. The air was expelled from the autoclave by purging with nitrogen, after which 259 grams of ethylene oxide was slowly introduced, under a vacuum, at a temperature of 125° C. This caused the pressure to rise to 3.0 bar. The reaction mixture was then stirred for another 30 minutes to ensure complete conversion of the ethylene oxide. These ethoxylated amidated rape oil fatty acids contained on average 0.9 ethylene oxide radicals.

EXAMPLE V 1813 grams of rape oil (Mw 894) and 653 grams of 2-(2-aminoethoxy)-ethanol (diglycolamine) (102 eq. %) were introduced into a 2 galon autoclave equiped with a stirrer, watercooling coil, nitrogen inlet, vacuum outlet, a heating jacket and a thermocouple. After expulsion of air from the autoclave by purging three times with vacuum and nitrogen the reaction mixture was heated to 50° C. Then 109 grams of a solution of $NaOCH_3$ (30% in methanol) was added slowly in 6 minutes. The autoclave was closed and the mixture was heated. After 30 minutes the temperature was increased to 125° C. and the pressure was raised to about 2 bar. After 90 minutes the pressure was decreased to 0.1 bar.

Subsequently the pressure was raised with nitrogen to +1.2 bar and the reaction mixture is cooled to 60° C. Then 2486 grams product was isolated and the degree of conversion was based on the diglycolamine, (2-(2-aminoethoxy)-ethanol): 94.3%.

EXAMPLE VI

In a 250 ml round bottom flask equiped with a mechanical stirrer, a nitrogen in- and outlet and a thermometer, 99.6 grams of coconut oil (Mw 664) was mixed with 48.2 grams of 2-(2-aminoethoxy)ethanol (102 eq. %) under nitrogen at room temperature. Then 6.0 grams of a solution of 30% $NaOCH_3$ in metanol was added at once. The reaction mixture was heated with a heating jacket to 125° C. for 2 hours. The aminolysis was stopped by cooling the flask in a waterbath. Then 149.3 grams of the coconutoildiglycolamide was isolated with a degree of conversion of 91.6 which solidified at 51° C.

EXAMPLE VII

In this example and the following examples VIII and IX the thickening effect of a number of thickeners according to the invention is evaluated in the manner described by Hensen et al. (loc. cit.; in particular page 380). From Hensen et al. (loc. cit.) it is known that the viscosity of a surfactant and/or a detergent surfactant containing a thickener is greatly affected by the concentration of NaCl. The viscosity increases with the NaCl content, reaches a maximum and then decreases again.

The thickening effect was determined of a detergent surfactant consisting of 26.5 wt. % Lauryl sulphate monoethanolamine salt, 7.0 wt. % of a product obtained from coconut oil by aminolysis followed by ethoxylation and then carboxymethylation, which, after dissolution in water to 34% dry substance, is commercially available as Akyposoft KA 250 BV, and 2.0 wt. % thickener, made up to 100% with demineralised water and NaCl. The maximum viscosity and the corresponding percentage of NaCl were determined at 20° C.

The rape oil fatty acid monoethanolamides of examples I and II, which had been ethoxylated with 1.6 and 1.3 ethoxy groups, respectively, were used as thickeners in these compositions. With both products the maximum viscosity was reached at an NaCl concentration of 3.0 wt. %. The maximum viscosity obtained with the ethoxylated rape oil fatty acid monoethanolamide product of example I (1.6 ethoxy groups) is 3930 mPa.s; that obtained with the ethoxylated rape oil fatty acid monoethanolamide product of example II (1.3 ethoxy groups) is 6500 mPa.s. At an NaCl concentration of 3.0 wt. % the viscosity of the composition without thickener is 725 mPa.s.

EXAMPLE VIII

Example VII was repeated with a detergent surfactant consisting of 42 wt. % of a 28 wt. % solution of lauryl diethoxyether sulphate sodium salt, which is commercially available as Akyposal EO 20 CP, and 2 wt. % thickener, made up to 100 wt. % with NaCl and water.

The ethoxylated rape oil fatty acid monoethanolamide product of example I (1.6 ethoxy groups) yielded a viscosity of 7500 mPa.s at an NaCl concentration of 2.5 wt. %. The ethoxylated rape oil fatty acid monoethanolamide product of example III (2.1 ethoxy groups) yielded a viscosity of 6100 mPa.s at an NaCl concentration of 2.5 wt. % and of 11000 mPa.s at an NaCl concentration of 3.0 wt. %. Without thickener, the viscosity was 60 mPa.s at 2.5 wt. % NaCl and 200 mPa.s at 3.0 wt. % NaCl.

EXAMPLE IX

Example VII was repeated with a detergent surfactant consisting of 30 wt. % of a 28 wt. % solution of lauryl diethoxyether sulphate sodium salt, which is commercially available as Akyposal EO 20 CP, 7 wt. % Akyposoft KA 250 BV and 2 wt. % thickener, made up to 100 wt. % with NaCl and water.

The ethoxylated rape oil fatty acid monoethanolamide product of example I (1.6 ethoxy groups) yielded a viscosity of 6700 mPa.s at an NaCl concentration of 3.0 wt. % and of 11000 mPa.s at a NaCl concentration of 3.5 wt. %. When the ethoxylated rape oil fatty acid monoethanolamide product of example III (2.1 ethoxy groups) was used as thickener, a viscosity of 6000 mPa.s, was obtained at an NaCl concentration of 3.0 wt. % and of 8500 mPa.s at an NaCl concentration of 3.5 wt. %.

Without thickener the viscosity of the composition is 70 mPa.s at 3.0 wt. % NaCl.

EXAMPLE X

Example VII was repeated with a detergent surfactant consisting of 16 wt. % of a 56 wt. % solution of parafine diethoxy ethersulphate (synthetic $C_{12}$–$C_{13}$ alkylethersulphate) which is commercially available as Akyposal DS 56 U/UK Spez., sodium salt (based on Dobanol), 5 wt. % of a 22 wt. % solution of lauryldecaethoxyethercarboxylate sodium salt (laureth-11 carboxylate sodium salt) which is commercially available as Akypo RLM 100 NV and 2.5 wt. % thickener, made up to 100 wt. % at pH 6 with NaCl water, and citric acid whereby the NaCl content is varied from 0.5 wt. % up to 3.0 wt. %. The experiment is carried out using 4 different types of thickeners: Thickener 1 is a rape oil diglycolamide product as described in example V, thickener 2 is a rape oil monoethanolamideethoxylate with 1,6 ethoxy groups, described in example I, thickener 3 is the commercially available product Aminol KDE which is a diethanolamide of coconutoil and diethanolamine, thickener 4 is a coconutoil-diglycolamide product as described in example VI. The viscosities of the compositions (pH=6) are given in table 1 in mPa.s.

TABLE 1

| % NaCl | thick. 1 | thick. 2 | thick. 3 | thick. 4 |
|---|---|---|---|---|
| 0.50 | 60 | 25 | 25 | — |

TABLE 1-continued

| % NaCl | thick. 1 | thick. 2 | thick. 3 | thick. 4 |
|---|---|---|---|---|
| 1.00 | 700 | 80 | 100 | 80 |
| 1.25 | 3,200 | 230 | 260 | 190 |
| 1.50 | 8,700 | 600 | 650 | 570 |
| 1.75 | 16,500 | 2,200 | 1,300 | 1,100 |
| 2.00 | 26,000 | 5,100 | 2,500 | 1,700 |
| 2.25 | 31,000 | 8,700 | 3,300 | 2,550 |
| 2.50 | 27,000 | 13,000 | 4,000 | 3,700 |
| 2.75 | 14,000 | 17,000 | 4,600 | 4,400 |
| 3.00 | 7,000 | 19,000 | 5,100 | 4,600 |

Table 1 shows that higher viscosities are obtained by using thickeners derived from rape oil, and that at lower NaCl content the maximum viscosity is reached. The best results are obtained in both respects by using thickener 1, the diglycolamide rape oil product of example V.

EXAMPLE XI

Example X was repeated with a surfactant mixture consisting of 26.50 wt. % of a 30 wt. % solution of lauryl sulphate monoethanolamine salt, which is commercially available as Akyposal MLS-30, 7.00 wt. % of a 30 wt. % solution of cococarboxamide monoethanolamide 4-carboxylate sodium salt, which is commercially available as Akypo KA-250-BV and at a NaCl concentration of 2.0%.

The results are given in table 2.

TABLE 2

| wt. % thick. | thick. 1 | thick. 2 | thick. 3 | thick. 4 |
|---|---|---|---|---|
| 0.25 | 130 | 110 | 55 | 50 |
| 0.50 | 250 | 180 | 90 | 80 |
| 0.75 | 690 | 260 | 135 | 110 |
| 1.00 | 1,500 | 340 | 180 | 170 |
| 1.25 | 2,500 | 980 | 340 | 300 |
| 1.50 | 3,800 | 1,700 | 540 | 450 |
| 1.75 | 5,300 | 2,400 | 760 | 600 |
| 2.00 | 7,000 | 3,300 | 1,000 | 800 |
| 2.25 | 9,200 | 3,950 | 1,500 | 1,360 |
| 2.50 | 11,000 | 4,700 | 1,800 | 1,750 |
| 2.75 | 9,200 | 5,000 | 2,250 | 2,200 |
| 3.00 | 5,600 | 5,200 | 2,500 | 2,400 |

Table 2 shows that using rape oil based thickeners, a higher viscosity is reached at lower thickener content. The best results are obtained using thickener 1.

EXAMPLE XII

Example XI was repeated with a detergent surfactant consisting of 26.8 wt. % of a 28 wt. % of a solution of Akyposal EO 20 CP as described in example IX, and 7.00 wt. % of Akyposoft KA-250 BV as described in example XI. The results are given in table 3. The same conclusions apply as in the previous example.

TABLE 3

| wt. % thick. | thick. 1 | thick. 2 | thick. 3 | thick. 4 |
|---|---|---|---|---|
| 0.50 | 300 | 80 | 30 | 25 |
| 0.75 | 500 | — | 50 | 40 |
| 1.00 | 900 | 250 | 110 | 85 |
| 1.25 | 2,100 | — | 185 | 135 |
| 1.50 | 6,600 | 660 | 230 | 210 |
| 1.75 | 14,000 | 1,300 | 360 | 320 |
| 2.00 | 27,000 | 2,800 | 660 | 650 |
| 2.25 | 37,000 | 7,000 | 1,250 | 1,300 |
| 2.50 | 36,000 | 12,000 | 2,200 | 2,400 |
| 2.75 | 15,000 | 17,000 | 2,760 | 3,200 |
| 3.00 | 5,600 | 16,000 | 3,200 | 3,700 |

We claim:
1. Composition comprising a mixture of amidated fatty acids or derivatives thereof with the formula

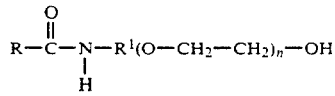

wherein $R^1$ is absent or an alkyl group with 2-4 C-atoms, the average value of n is 0.5 to 3, and R represents a mixture of fatty acid radicals with 14-24 C-atoms, obtained by aminolysing and ethoxylating oils produced from the plant species "Brassica" with an eruca acid content lower than 5%.

2. Mixture according to claim 1, wherein $R^1$ is an ethyl or an isopropyl group.

3. Mixture according to claim 1 or 2, wherein the averaged value of n is 1-2.

4. Composition comprising a mixture of amidated fatty acids, or derivatives thereof, with the formula

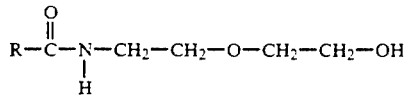

wherein R represents a mixture of fatty acid radicals with 14-24 C-atoms, obtained by aminolysing rape oils, produced from the plant species "Brassica" with an eruca acid content lower than 5%, with 2-(2-aminoethoxy)ethanol.

5. Composition comprising a mixture of amidated fatty acids or derivatives thereof with the formula

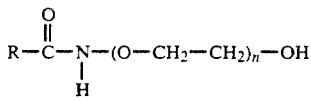

wherein the average value of n is 0.5 to 3 and R represents a mixture of fatty acid radicals with 14-24 C-atoms obtained by aminolysing and ethoxylating rape oils produced from the plant species 'Brassica' with an eruca acid content lower than 5%.

6. Thickener consisting essentially of a mixture according to claims 1, 4 or 5.

7. Detergent composition containing one or more thickeners according to claim 6.

8. Detergent composition comprising one or more thickeners comprising a mixture of amidated fatty acids or derivatives thereof with the formula

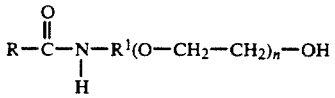

wherein R' is absent or an alkyl group with 2-4 C-atoms, the average value of n is 0.5 to 3 and R represents a mixture of fatty acid radicals with 14-24 C-atoms obtained by aminolysing and ethoxylating rape oil produced from the plant species 'Brassica' with an eruca acid content lower than 5%, said thickener giving a maximum viscosity of at least 300 mPa.s, the thickener concentration being 0.25-5%, and said surfactant or detergent or composition further including NaCl at a concentration of less than 5%.

* * * * *